United States Patent [19]

Schmitt et al.

[11] Patent Number: 4,695,552
[45] Date of Patent: Sep. 22, 1987

[54] PROCESS AND REAGENT FOR THE DETERMINATION OF THE HEMOGLOBIN-HAPTOGLOBIN COMPLEX IN THE PRESENCE OF FREE HEMOGLOBIN

[75] Inventors: Urban Schmitt, Tutzing; Rolf Deeg, Bernried; Joachim Ziegenhorn, Starnberg, all of Fed. Rep. of Germany

[73] Assignee: Boehringer Mannheim GmbH, Mannheim, Fed. Rep. of Germany

[21] Appl. No.: 601,801

[22] Filed: Apr. 19, 1984

[30] Foreign Application Priority Data

Apr. 20, 1983 [DE] Fed. Rep. of Germany ....... 3314308

[51] Int. Cl.$^4$ .......................... G01N 33/72; C12Q 1/28
[52] U.S. Cl. ........................................ 436/66; 436/67; 436/175; 435/28
[58] Field of Search ...................... 435/28, 4, 269, 810, 435/184; 436/66, 67, 175

[56] References Cited

U.S. PATENT DOCUMENTS 4,353,984  10/1982  Yamada et al. ...................... 435/28
4,517,287   5/1985  Scheibe et al. ...................... 435/28

FOREIGN PATENT DOCUMENTS 0095302  11/1983  European Pat. Off. .............. 435/28

OTHER PUBLICATIONS

Kawamura, K. et al., *Biochim. Biophys. Acta.*, 285 (1972), pp. 22–27.
Sawicki, E. et al. *Anal. Chem.*, vol. 33, No. 6, May 61, pp. 722–725.

*Primary Examiner*—Esther M. Kepplinger
*Attorney, Agent, or Firm*—Felfe & Lynch

[57] ABSTRACT

The present invention provides a process for the determination of the hemoglobin-haptoglobin complex in the presence of free hemoglobin by utilization of the different peroxidate properties of free and of bound hemoglobin, wherein, for the selective inhibition of the peroxidase activity of the free hemoglobin, a detergent is added and the residual peroxidate activity of the reaction mixture is measured.

The present invention also provides a reagent for carrying out this process wherein, besides the substances required for the determination of the peroxidase activity, it contains a detergent for the inhibition of the peroxidase activity of free hemoglobin.

Furthermore, the present invention provides a process for determining the haptoglobin content of a sample, as well as a process for determining glycosilated hemoglobin in a sample.

14 Claims, 1 Drawing Figure

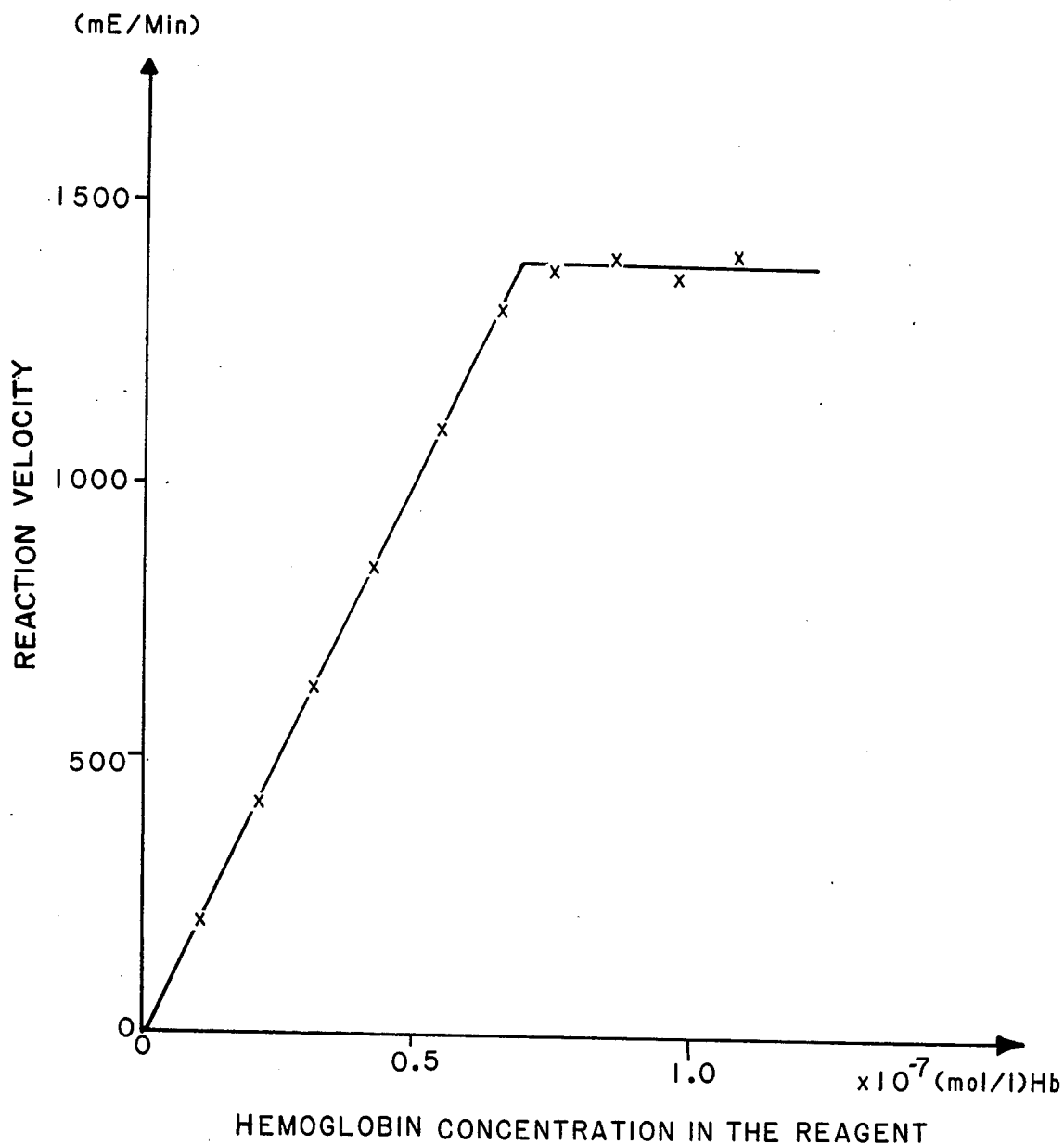

PROCESS AND REAGENT FOR THE DETERMINATION OF THE HEMOGLOBIN-HAPTOGLOBIN COMPLEX IN THE PRESENCE OF FREE HEMOGLOBIN

The present invention is concerned with a process and a reagent for the determination of the hemoglobin-haptoglobin complex in the presence of free hemoglobin.

Hemoglobin possesses peroxidase activity which is also retained in the hemoglobin-haptoglobin complex. The determination of hemoglobin via its peroxidase activity is substantially more sensitive than the direct photometric determination of appropriate hemoglobin derivatives, for example of cyanomethemoglobin. The peroxidase activity of free hemoglobin and of the hemoglobin-haptoglobin complex can be influenced in different ways, for example by changing the pH value.

For the measurement of the peroxidase activity of free hemoglobin and of the hemoglobin-haptoglobin complex, two different measurement principles have been described (cf. in this regard: Z. Klin. Chem. u. Klin. Biochem., 6, 69–112/1968, as well as Biochim. Biophys. Acta, 285, 22–27/1972):

(a) The solution to be determined, containing hemoglobin or the hemoglobin-haptoglobin complex, is mixed with hydrogen peroxide and with an appropriate chromogenic substrate and incubated up to the end of the color development. The end of the reaction comes about by the hemoglobin being inactivated by the hydrogen peroxide. The maximum extinction achieved is measured. After reaching this maximum, the extinction often decreases again as a result of the instability of the coloured material formed.

(b) The reaction velocity of the reaction between hemoglobin or hemoglobin-haptoglobin complex, hydrogen peroxide and chromogenic substrate is measured at the beginning of the reaction (initial velocity).

Disadvantages of method (a) in the determination of the haemoglobin-haptoglobin complex are, inter alia, that there is no linear relationship between the measured value and the concentration of the complex and the free hemoglobin shows, depending upon the hydrogen peroxide concentration used, either a higher or a lower activity than the complex.

In the case of the determination of the complex concentration in the presence of free hemoglobin method (b) is to be preferred to method (a) since, in the case of the latter, there is a linear relationship between the measurement value and the concentration of the hemoglobin-haptoglobin complex and in the case of a displacement of the pH value into the acidic range, the peroxidase activity of the complex is always higher than that of the free hemoglobin.

The accuracy of the measurement depends decisively upon the differentiation of the peroxidate activity of hemoglobin in free and bound form. In the case of the previously described methods of determination, use has essentially been made of the differing influencing of the peroxidase activity by change of the pH value. The ratio of activities of equal molar amounts of complex and of free hemoglobin is, at a pH value of about 4, 10:1 to 20:1. It depends upon the chromogenic substrate employed and upon the substrate and hemoglobin concentration used. The residual activity of the free hemoglobin always present prevents a dependable and exact measurement of the concentration of hemoglobin haptoglobin complex but especially when more free hemoglobin is present than hemoglobin bound in the complex.

It is an object of the present invention to provide a process for the determination of hemoglobin-haptoglobin complex in the presence of free hemoglobin in which the peroxidase activity of the free hemoglobin is substantially inactivated and the peroxidase activity of the hemoglobin haptoglobin complex can be measured undisturbed and thus exactly.

This object is achieved by adding to the reaction mixture a detergent which almost completely inactivates the peroxidase activity of the free hemoglobin but does not change or only insubstantially changes the peroxidase activity of the hemoglobin bound in the complex.

Thus, according to the present invention, there is provided a process for the determination of the hemoglobin-haptoglobin complex in the presence of free hemoglobin by utilization of the different peroxidase properties of free and of bound hemoglobin, wherein, for the selective inhibition of the peroxidase activity of the free hemoglobin, a detergent is added and the residual peroxidase activity of the reaction mixture is measured.

According to the present invention, use can be made of all detergents which inactivate the free peroxidase activity of the free hemoglobin as completely as possible but do not noticeably influence the peroxidase activity of the bound hemoglobin and which also do not suppress the peroxidate colored material formation. Detergents from the saponin and lanolin groups and detergents with a sugar or sugar alcohol component have proved to be especially useful. Especially preferred according to the present invention are saponin, digitonin and polyoxyethylene-sorbitol, for example the detergent G 2330 of the firm Atlas.

Saponins are generally to be understood to belong to a group of vegetable glycosides which form colloidal, soap-like solutions in water. The aglycones of these glycosides possess triterpenoid or steroid structures. Digitonin, a digitalis glycoside, as well as the commercially available saponin, the component materials of soapwort and of Panama bark generally consisting of saponins, belong to this group of detergents.

The lanolins are complex constituted ester mixtures of fatty acids, for example palmitic acid, caproic acid, oleic acid and the like, and aliphatic, triterpenoid or steroid alcohols, for example cetyl alcohol, cholesterol, lanosterol and the like. These ester mixtures become enriched in sheep wool and are obtained therefrom.

The peroxidase activity can also be determined in known manner after addition of a detergent. For this purpose, a series of processes are available to the expert. In general, a peroxide is added to the solution to be determined and a substrate added thereto which, by the action of the peroxidase and of the peroxide, undergoes a characteristic, easily measurable color change.

For the determination of the hemoglobin-haptoglobin complex in the presence of free hemoglobin, to the sample containing the complex and free hemoglobin there is preferably added the detergent, a chromogenic substrate and an appropriate buffer system, as well as possibly further adjuvant materials, the peroxidase reaction being started by the addition of a peroxide and the change of extinction being measured photometrically. The reaction velocity is expressed as the change of extinction per unit time ($\Delta E$/min.).

The concentration of the detergent can be freely selected within wide limits. The amount employed depends essentially upon which detergent is used and which differentiation of the peroxidase activity is to be achieved in order to obtain a usable, exact measurement value with the chosen peroxidase detection system. Upwardly, the usable concentration of the detergent is limited by its solubility in the reaction solution. If this maximum solubility is exceeded, then turbidities occur which impair the determination process or make it impossible.

The chromogenic substrates used are those which can be reacted by peroxidases in an acidic medium with peroxide. Guaiacol and 2,2'-azino-di(3-ethylbenzthiazoline-6-sulphonic acid) (ABTS), as well as the two-component systems 4-aminoantipyrine (AAP) and 3-methyl-2-benzthiazolone hydrazone (MBTH) or 3-methyl-2-benzthiazolone hydrazone sulphonic acid (SMBTH) in combination with a phenol or aniline derivative (cf. Analytical Chemistry, 33, 722–725/1961) have proved to be especially useful. The chromogenic substrate is usually employed in a concentration of 0.1 to 50.0 mmol/liter and depends essentially upon the selected substrate. Thus, the preferred concentration for ABTS and AAP is from 0.1 to 5 mmol/liter, for guaiacol is from 1 to 50 mmol/liter and for MBTH and SMBTH is from 0.1 to 1 mmol/liter. The phenol or aniline derivatives are, in the case of the two-component systems, used in an approximately 10 fold higher concentration than the corresponding coupling partner.

The buffer systems used are all those with a buffer action which lies in the acidic pH range, for example acetate buffer, citrate buffer and the like. Especially useful according to the present invention are citrate buffers with a buffer action in the range of pH 3.5 to 4.5, a citrate buffer with a pH of 3.8 to 4.0 being especially preferred. The buffer concentration is in the range of from 0.001 to 0.5 mol/liter and is preferably 0.01 to 0.2 mol/liter.

The peroxide used is preferably hydrogen peroxide or a perborate. The concentration of the peroxide in the test solution should be 0.1 to 100 and preferably 0.5 to 25 mmol/liter.

The process of determination is usually carried out at a temperature of from 20° to 45° C. and preferably of from 25° to 30° C.

The sample to be determined should have a hemoglobin concentration of from $0.5 \times 10^{-8}$ to $2 \times 10^{-7}$ mol/liter.

The present invention also provides a reagent for the determination of the hemoglobin-haptoglobin complex in the presence of free hemoglobin which, besides the substances usually necessary for the determination of the peroxidase activity, contains a detergent which inhibits the peroxidase activity of the free hemoglobin. Such a reagent preferably contains a detergent selected from the group consisting of saponins, lanolins and the detergents with a sugar or sugar alcohol component, as well as substances for the detection of the peroxidase activity, a peroxide, a chromogenic substrate, an appropriate buffer system and possibly further adjuvants.

A preferred reagent according to the present invention contains the above-mentioned components in the following concentrations:
0.1–50 g./liter detergent
0.1–100 mmol/liter peroxide
0.1–5 mmol/liter chromogenic substrate
0.001–0.5 mol/liter buffer.

An especially preferred reagent according to the present invention has the following composition:
1–5 g./liter saponin
0.5–25 mmol/liter perborate
0.5–2 mmol/liter ABTS
0.01–0.2 mol/liter citrate buffer (pH 3.5–4.5).

The process according to the present invention can also be utilized in advantageous manner for the determination of haptoglobin by completely converting the haptoglobin into the hemoglobin-haptoglobin complex by the addition of an excess of hemoglobin, the concentration of the complex being measured by the process according to the present invention. The added amount of hemoglobin is bound by the haptoglobin to give a haptoglobin-hemoglobin complex until the total amount of haptoglobin in the sample is present as the complex, excess hemoglobin remaining in solution as free hemoglobin. In the case of the measurement of the peroxidate activity by the process according to the present invention, this does not contribute to an extinction increase since the peroxidase activity of the free hemoglobin is substantially inactivated by the added detergent. The measured extinction corresponds to the concentration of haptoglobin-hemoglobin complex and thus to the haptoglobin concentration originally present in the sample.

The process according to the present invention for the measurement of the haptoglobin-hemoglobin complex in the presence of free hemoglobin can also be employed in an advantageous manner for the determination of glycosylated hemoglobin according to the process described and claimed in German Patent Specification No. 31 41 146. For this purpose, the sample to be determined is mixed with haptoglobin for the differentiation of the glycosylated and non-glycosylated portion. Haptoglobin forms a complex with glycosylated hemoglobin more quickly than with the non-glycosylated hemoglobin. The glycosylated hemoglobin-haptoglobin complex can be detected on the basis of its peroxidase activity.

Normally, the concentration of glycosylated hemoglobin in the blood amounts to 5% but in the case of diabetics, this concentration is increased to up to 20%. Thus, in a sample mixed with haptoglobin, the glycosylated hemoglobin-haptoglobin complex is present, besides a large excess of free hemoglobin. The addition, according to the present invention, of a detergent which inactivates the peroxidase activity of the free hemoglobin but leaves that of the portion bound to haptoglobin uninfluenced, here proves to be quite especially useful. In this way, it is possible to determine the peroxidase activity of the glycosylated hemoglobin-haptoglobin complex sufficiently accurately, without having to separate off the free hemoglobin in the sample.

An advantageous embodiment of this process of determination consists in separating off the erythrocytes from the sample, for example whole blood, and hemolysing, mixing the hemolysate with dithionite up to a concentration of 10 to 100 mg./ml. and with nitrite up to a concentration of 0.2 to 10 mg./ml. and adjusting to a hemoglobin concentration of about 0.5 mg./liter with a buffer solution (pH 5.5 to 7.0) or with a buffer solution (pH 5.5 to 7.0) which contains a compound with a binding action on the allosteric effector places of the hemoglobin, for example inositol hexaphosphate, 2,3-diphosphoglycerate and the like, in a concentration of 0.04 to 0.2 mmol/liter. One part by volume of this hemoglobin sample is mixed with one part by volume of a reagent solution which contains 5 to 50 mmol/liter of buffer (pH 5.5 to 7.0), 10 to 50 mg./liter haptoglobin, 0.1 to 0.4 g./ml. saccharose and 0.2 to 50.0 mmol/liter of chromogenic substrate. The peroxidase reaction is started by the addition of a solution which contains a peroxide and the detergent used according to the present invention. The peroxidase reaction is monitored by measurement of the extinction increase at the wavelength characteristic for the chromogenic substrate used, the reaction velocity, expressed in mE/min., being determined.

The above-described determination process is also especially suitable for carrying out in an automatic analyzer.

The following Examples are given for the purpose of illustrating the present invention:

EXAMPLE 1

2 ml. of a reagent solution containing 0.1 mol/liter sodium citrate buffer (pH 3.8) and 1 mmol/liter ABTS are mixed with 0.025 ml. of a sample solution which contains free hemoglobin or the hemoglobin haptoglobin complex, the hemoglobin concentration in the sample being, in each case, 0.25 mg. hemoglobin/ml. The peroxidase reaction is started by the addition of 0.020 ml. of 0.58 molar sodium perborate solution in 0.15 molar citric acid and the colour development is monitored by extinction measurement at 436 nm (Eppendorf photometer with attached recorder). The reaction temperature is 25° C.

The same measurements are carried out with reagent solutions which, besides the above-mentioned sodium citrate buffer and the ABTS, additionally contain saponin in increasing concentrations. The reaction velocities ($\Delta$E/min.) measured for the free hemoglobin and for the hemoglobin-haptoglobin complex without detergent and at different saponin concentrations are given in the following Table 1.

TABLE 1

Reaction velocities ($\Delta$E/min.) for the peroxidase reaction of free hemoglobin (Hb) and of hemoglobin haptoglobin complex (Hb:Hp) with perborate and ABTS as substrate at different saponin concentrations

| ABTS [mmol/l.] | saponin [mg./ml.] | $\Delta$E/min. Hb [mE/min.] | $\Delta$E/min. Hb:Hp [mE/min.] | Hb:Hp Hb |
| --- | --- | --- | --- | --- |
| 1 | — | 172 | 968 | 5.6 |
| 1 | 0.5 | 75 | 1003 | 13.4 |
| 1 | 1.0 | 57 | 1003 | 17.4 |
| 1 | 2.0 | 48 | 968 | 20.4 |
| 1 | 3.0 | 40 | 932 | 23.3 |
| 1 | 4.0 | 30 | 1003 | 33.4 |
| 1 | 5.0 | 15 | 1003 | 66 |

Without the addition of saponin, at a pH value of 3.8, the reactivity of the free hemoglobin is smaller than the reactivity of the complex merely by a factor of 1:5.6. It can be seen from Table 1 that, by means of increasing saponin additions, the peroxidase activity of the free hemoglobin is clearly lowered, whereas the activity of the complex does not alter markedly. If saponin is added in an amount of 5 mg./ml., then the activity of the free hemoglobin is lowered to one tenth of its initial value. The ratio of the peroxidase activity of the free hemoglobin to the complex then amounts to 1:66.

EXAMPLE 2

2 ml. of reagent containing 0.1 mol/liter sodium citrate buffer (pH 3.8) and 0.5 mmol/liter ABTS are mixed with 0.025 ml. of a sample which contains free hemoglobin or hemoglobin-haptoglobin complex with a hemoglobin concentration of 0.25 mg. hemoglobin/ml. It is further worked up as described in Example 1. Analogous measurements are carried out with reagent solutions to which saponin has been added in differing concentrations. The measurement values found are summarized in the following Table 2.

TABLE 2

Reaction velocities ($\Delta$E/min.) of the peroxidase reaction between free hemoglobin and hemoglobin haptoglobin complex, with perborate and ABTS as substrate, in the presence of different saponin concentrations

| ABTS [mmol/l.] | saponin [mg./ml.] | $\Delta$E/min. Hb [mE/min.] | $\Delta$E/min. Hb:Hp [mE/min.] | Hb:Hp Hb |
| --- | --- | --- | --- | --- |
| 0.5 | — | 78.8 | 1285 | 16.3 |
| 0.5 | 0.5 | 32[1] | 1175 | 70 |
| 0.5 | 1.0 | 7.5 | 1175 | 150 |
| 0.5 | 3.0 | 12.5[2] | 1175 | 375 |
| 0.5 | 5.0 | 30[3] | 873 | 230 |

[1]hemoglobin concentration 0.50 mg. Hb/ml.
[2]hemoglobin concentration 1.00 mg. Hb/ml.
[3]hemoglobin concentration 2.00 mg. Hb/ml.

The values given in Table 2 show that at a comparatively low ABTS concentration, the reactivity differences between free hemoglobin and hemoglobin-haptoglobin complex are comparatively large without the addition of a detergent. By means of the addition of saponin, the peroxidase activity of the free hemoglobin is almost completely inactivated. In order to obtain still good measurable values, the hemoglobin concentrations must be increased up to the eightfold value in comparison with the concentrations employed in Example 1.

EXAMPLE 3

2 ml. of a reagent solution containing 0.1 mol/liter of sodium citrate buffer (pH 3.8) and 0.5 mmol/liter ABTS are mixed with 0.025 ml. of a sample solution which contains free hemoglobin or the hemoglobin-haptoglobin complex with a hemoglobin concentration of 0.25 mg. Hb/ml. The peroxidase reaction is started with 0.020 ml. of 0.58 molar sodium perborate solution in 0.15 molar citric acid and the color development is monitored by extinction measurement at 436 nm. The reaction temperature is 25° C.

Analogous measurements are carried out in which, in addition to the above-mentioned components, there are added to the reagent solution the detergents mentioned in the following Table 3 in the concentrations there also given. The measurement values are summarized in Table 3.

TABLE 3

Reaction velocities ($\Delta$E/min.) of the peroxidase reaction for free hemoglobin and hemoglobin haptoglobin complex with peroxide and ABTS as substrate in the presence of different detergents

| ABTS [mmol/l.] | detergent [mg./ml.] | $\Delta$E/min. Hb [mE/min.] | $\Delta$E/min. Hb:Hp [mE/min.] | Hb:Hp Hb |
| --- | --- | --- | --- | --- |
| 0.5 | — | 55 | 1002 | 18.2 |
| 0.5 | 0.15 digitonin | 21.8 | 818 | 37.6 |
| 0.5 | 0.3 digitonin | 20 | 818 | 41 |
| 0.5 | 20 G2330[1] | 8.8 | 845 | 97 |
| 0.5 | 40 G2330[1] | 0-5 | 873 | >100 |

[1]G 2330 = polyoxyethylene sorbitol detergent of the firm Atlas

EXAMPLE 4

2 ml. of a reagent solution containing 0.1 mol/liter of sodium acetate buffer (pH 4.0) and 30 or 15 mmol/liter of guaiacol are mixed with 0.05 ml. of a sample solution which contains free hemoglobin or a hemoglobin-haptoglobin complex with a hemoglobin concentration of 0.25 mg. Hb/ml. The peroxidase reaction is started with 0.1 ml. of 0.58 molar sodium perborate solution in 0.15 molar citric acid and the color development is monitored by extinction measurement at 436 nm. The reaction temperature is 25° C. After a certain time, the color development comes to a stop. Because of the instability of the colored material, the extinction again decreases. The extinction changes given in the following Table 4 are the initial velocities determined by plotting the tangents on the extinction-time curves.

Analogous measurements are carried out in which, to the reagent solution, there has been added, in each case, one of the detergents given in Table 4 in the there-given concentration. The results found are summarized in the following Table 4.

TABLE 4

Reaction velocities ($\Delta E$/min.) of the peroxidase reaction for hemoglobin and hemoglobin haptoglobin complex with peroxide and guaiacol as substrate in the presence of different detergents

| guaiacol [mmol/l.] | detergent [mg./ml.] | Hb [mE/min.] | Hb:Hp [mE/min.] | Hb:Hp / Hb |
|---|---|---|---|---|
| 30 | — | 17 | 200 | 11.8 |
| 30 | 0.5 saponin | 0 | 164 | >106 |
| 30 | 1.0 | 0 | 138 | >100 |
| 30 | 5 | 0 | 96 | >100 |
| 30 | 1.0 | 6[2] | 138 | 90 |
| 30 | 2.0 | 5.5[2] | 138 | 100 |
| 15 | — | 60 | 169 | 2.8 |
| 15 | 2.0 saponin | 0 | 115 | >100 |
| 30 | — | 14.5 | 194 | 13.4 |
| 30 | 40 G2330[1] | 10 | 145 | 14.5 |
| 30 | 0.5 digitonin | 3 | 154 | 50 |

[1] G 2330 = polyoxyethylene sorbitol detergent of the firm Atlas
[2] hemoglobin concentraton 1.00 mg. Hb/ml.

EXAMPLE 5

Titration of a haptoglobin-containing sample with hemoglobin

A haptoglobin stock solution in water is prepared. Aliquots of this stock solution are incubated with different, exactly known amounts of hemoglobin for 10 minutes at ambient temperature. Samples of the pre-incubated mixtures are transferred into the same amounts of a reagent solution which contains 0.1 mol/liter of sodium citrate buffer (pH 4.0), 0.5 mmol/liter ABTS and 3 g./liter saponin. The end concentration of the haptoglobin in the cuvette is $0.64 \times 10^{-7}$ mol/liter. The peroxidase reaction is started by the addition of sodium perborate solution (end concentration in the cuvette 5 mmol/liter) and the reaction velocity is measured by way of the formation of a green colored material (wavelength 436 nm).

In FIG. 1 of the accompanying drawings, there is plotted the reagent velocity in dependence upon the hemoglobin concentration in the reagent. From FIG. 1, it can be seen that the reaction velocity increases linearly with increasing hemoglobin concentration until the haptoglobin present in the solution is completely present as hemoglobin-haptoglobin complex. Hemoglobin addition over and above this saturation concentration no longer leads to a clearly measurable higher reaction velocity.

EXAMPLE 6

Determination of glycosylated hemoglobin (a) Reagents used:
Reagent Ia:
  50 mmol/liter bis-tris buffer (pH 6.7)
Reagent Ib:
  50 mmol/liter bis-tris buffer (pH 6.7)
  0.08 mmol/liter inositol hexaphosphate
Reagent II:
  7 mmol/liter bis-tris buffer (pH 6.7)
  2 mmol/liter ABTS
  20 mg./liter haptoglobin
  0.2 g./ml. saccharose
Reagent III:
  0.5 mol/liter citrate buffer (pH 3.8)
  30 mmol/liter sodium perborate
  3 g./liter saponin.

(b) Carrying out of experiment

Erythrocytes are centrifuged off from a sample of whole blood to be measured, washed three times with physiological sodium chloride solution and haemolysed by the addition of the same volume of water. The hemolysate is mixed with solid sodium dithionite up to a concentration of 50 mg./ml. and with solid sodium nitrite up to a concentration of 5 mg./ml. After a short incubation at ambient temperature, an aliquot of the pre-treated hemolysate is adjusted with reagent Ia or reagent Ib to a hemoglobin concentration of 0.5 mg./ml. The so obtained sample solution is placed into the sample vessel of an automatic analysis apparatus, for example Abbott VP. In each case, the apparatus mixes 2.5 $\mu$l. of the sample solution with 2.5 $\mu$l. of reagent solution II. It is incubated for 40 seconds at 25° C. and thereafter the peroxidase reaction is started by the addition of 150 $\mu$l. of reagent III. The extinction increase is monitored with the filter combination 415/450 nm for 2 minutes and the reaction velocity is expressed as the quotient observed extinction change/2 minutes in mE/min.

The reaction velocity obtained in the case of the addition of reagent Ib to the sample is divided by the one measured with reagent Ia.

By analogous measurements and evaluations of standard samples with known contents of glycosylated hemoglobin, there is produced a calibrated curve from which the concentration of glycosylated hemoglobin in unknown samples can be read off.

The following Table 5 gives the values for four different samples determined in the above-described manner (method A) (column 2). For comparison, in column 3 are given the corresponding values which have been obtained according to the hitherto usual method by chromatography on haptoglobin-containing ion exchange columns (method B). The values show a good agreement.

TABLE 5

Content of glycosifated hemoglobin (HbA$_1$) in different samples (A) measured after the addition of a detergent according to the present invention (B) measured by chromatography on ion exchange columns

| sample No. | method A [%] HbA$_1$ | method B [%] HbA$_1$ |
|---|---|---|
| 1 | 7.5 | 7.3 |
| 2 | 16.4 | 16.0 |

TABLE 5-continued

Content of glycosifated hemoglobin (HbA$_1$) in different samples
(A) measured after the addition of a detergent
according to the present invention
(B) measured by chromatography on ion exchange columns

| sample No. | method A [%] HbA$_1$ | method B [%] HbA$_1$ |
| --- | --- | --- |
| 3 | 8.8 | 8.9 |
| 4 | 11.2 | 12.9 |

It will be understood that the specification and examples are illustrative but not limitative of the present invention and that other embodiments within the spirit and scope of the invention will suggest themselves to those skilled in the art.

What is claimed is:

1. A process for the determination of the hemoglobin-haptoglobin complex in a sample containing free hemoglobin comprising the steps of adding a detergent to the sample to be determined, in an effective amount to almost completely inactivate the peroxidase activity of the free hemoglobin without substantially changing the peroxidase activity of the hemoglobin-haptoglobin complex, and thereafter measuring the residual peroxidase activity of the reaction mixture as a measure of the amount of hemoglobin-haptoglobin complex.

2. The process of claim 1, wherein the detergent is selected from the group consisting of the saponins, lanolins and detergents with a sugar component.

3. The process of claim 2, wherein saponin, digitonin or polyoxyethylene-sorbitol detergent is used as the detergent.

4. The process of claim 2 wherein 0.1 to 50 grams/liter detergent is used.

5. The process of claim 1 wherein 0.1 to 50 grams/liter detergent is used.

6. The process of claim 1 wherein a peroxide and a chromogenic substrate is used for the measurement of the peroxidase activity.

7. Process according to claim 6, wherein guaiacol or 2,2'-azino-di-(3-ethylbenzthiazoline-6-sulphonic acid is used as the chromogenic substrate.

8. Process according to claim 6, wherein said chromogenic substrate is 4-aminoantipyrine, 3-methyl-2-benzthiazolone hydrazone or 3-methyl-2-benzthiazolone-hydrazone sulphonic acid, in combination with a phenol or aniline derivative.

9. A process for the determination of haptoglobin content of a sample, comprising mixing the sample with an excess of hemoglobin, and thereafter determining the hemoglobin-haptoglobin complex by the process of claim 1.

10. Process for the determination of glycosylated hemoglobin in a sample by differentiation of glycosylated and non-glycosylated hemoglobin with the use of haptoglobin and thereafter measuring the peroxidase activity of the glycosylated hemoglobin-haptoglobin complex with the process of claim 1.

11. A reagent for determining the hemoglobin-haptoglobin complex in the presence of free hemoglobin comprising means for the determination of the peroxidase activity of said hemoglobin-haptoglobin complex and a detergent selected from the group consisting of saponins and lanolins for the inhibition of the peroxidase activity of free hemoglobin, wherein said detergent is present in an amount effective to almost completely inactivate the peroxidase activity of said free hemoglobin without substantially changing the peroxidase activity of said hemoglobin-haptoglobin complex.

12. The reagent of claim 11, wherein saponin or digitonin is used as the detergent.

13. The reagent of claim 11, containing
0.1–50 g./liter detergent
0.1–100 mmol/liter peroxide
0.1–5 mmol/liter chromogenic substrate
0.001–0.5 mol/liter buffer.

14. The reagent of claim 13, containing
1–5 g./liter saponin
0.5–25 mmol/liter perborate
0.5–2 mmol/liter 2,2'-azino-di(3-ethylbenzthiazoline-6-sulfonic acid)
0.01–0.2 mol/liter citrate buffer, pH 3.5–4.5.

* * * * *